United States Patent
Chasar et al.

(10) Patent No.: US 6,891,053 B2
(45) Date of Patent: May 10, 2005

(54) METHOD OF MAKING OLEOCHEMICAL OIL-BASED POLYOLS

(75) Inventors: Dwight W. Chasar, Sagamore Hills, OH (US); Michael J. Hughes, Hinckley, OH (US)

(73) Assignee: Noveon IP Holdings Corp., Cleveland, OH (US)

( * ) Notice: Subject to any disclaimer, the term of this patent is extended or adjusted under 35 U.S.C. 154(b) by 158 days.

(21) Appl. No.: 09/969,059

(22) Filed: Oct. 2, 2001

(65) Prior Publication Data

US 2003/0088054 A1 May 8, 2003

(51) Int. Cl.$^7$ .................................................. C11C 1/00
(52) U.S. Cl. ........................................................ 554/168
(58) Field of Search ............................................ 554/168

(56) References Cited

U.S. PATENT DOCUMENTS

| | | | |
|---|---|---|---|
| 4,133,799 A | 1/1979 | Layer | |
| 4,474,602 A | 10/1984 | Markley et al. | |
| 4,508,853 A * | 4/1985 | Kluth et al. | 521/107 |
| 4,546,120 A | 10/1985 | Peerman et al. | |
| 4,551,517 A | 11/1985 | Herold et al. | |
| 4,742,087 A | 5/1988 | Kluth et al. | |
| 4,826,944 A | 5/1989 | Hoefer et al. | |
| 4,886,893 A | 12/1989 | Meffert et al. | |
| 5,266,714 A | 11/1993 | Stoll et al. | |
| 5,302,626 A | 4/1994 | Heofer et al. | |
| 5,672,752 A | 9/1997 | Lai et al. | |
| 5,750,787 A | 5/1998 | Lai et al. | |
| 6,107,433 A * | 8/2000 | Petrovic et al. | 528/1 |
| 6,433,121 B1 * | 8/2002 | Petrovic et al. | 528/1 |

FOREIGN PATENT DOCUMENTS

EP      554590    *   8/1993

* cited by examiner

*Primary Examiner*—Deborah D. Carr
(74) *Attorney, Agent, or Firm*—Joe A. Powell; Thoburn T. Dunlap; George W. Moxon, II

(57) ABSTRACT

A method of making oleochemical oil-based polyols by mixing an acid activated or acid leached clay, an epoxidized oleochemical oil, alcohol, and acid activated or acid leached clay so the epoxidized oleochemical oil reacts with said alcohol to form a oleochemical oil-based polyol, filtering out said clay, stripping off any excess alcohol, and recovering the oleochemical oil-based polyol.

11 Claims, No Drawings

METHOD OF MAKING OLEOCHEMICAL OIL-BASED POLYOLS

BACKGROUND OF THE INVENTION

The present invention relates to a method for making oleochemical oil-based polyols using acid treated clay catalysts. The oleochemical oil-based polyols can be used to produce polyurethane resins for a variety of uses.

Polyols may be produced from petroleum. However, polyols made from oleochemical oils would be preferred since they come from renewable resources. Oleochemical oils are produced from the fats and oils of, for example, beef tallow, palm oil, lard, castor oil, peanut oil, rapeseed oil, cottonseed oil, soya bean oil, sunflower oil, and linseed oil. Oleochemical oil molecules must be chemically transformed in order to introduce hydroxyl groups. For instance, soybean oil does not contain any hydroxyl groups but has on an average about 4.6 double bonds per molecule. The unsaturated portions of the vegetable oil molecule can be converted to hydroxyl groups. However, many reactions for preparing polyols from vegetable oils are not very selective. By-products, in addition to alcohol groups, are created during the transformation. Furthermore, many conventional methods of preparing polyols from vegetable oil do not produce polyols having a significant content of hydroxyl groups, and many available methods of preparing polyols from vegetable oils do not produce products having a desirable viscosity. Greases or waxes often result as a consequence of such chemical transformations.

Vegetable oil-based polyols are known. For example, U.S. Pat. No. 6,107,433 to Petrovic, et al. discloses a process for converting vegetable oil into polyols by epoxidizing the oil using a fluoboric acid catalyst and then hydroxylating the epoxidized oil to a polyol using more fluoboric acid catalyst plus an alcohol or an alcohol and water, which is preferred. The problem with the process is that the fluoboric acid is expensive, highly reactive, hazardous to handle, and highly exothermic, must be quenched, and its byproducts present disposal problems. The polyols can be used to make polyurethane resins.

Polyurethane resins prepared with castor oil have also been produced. However, these resins tend to be rubbery and thus undesirable for certain casting applications. Still further, castor oil-based polyurethanes have some limitations due to their higher price and environmental problems related to their by-products. For example, U.S. Pat. No. 4,508,853 to Kluth, et al. teaches the preparation of polyurethane prepolymers containing terminal isocyanate groups in which oleochemical polyols are present as the polyol component. The polyols are made by subjecting epoxidized triglycerides to ring opening using acid catalysis such as mineral acids, including sulfuric acid, phosphoric acid, hydrochloric acid, or organic acids such as sulfonic acids, including p-toluene sulfonic acid. Other examples of urethanes incorporating fatty polyols made by acid catalyzed hydroxylation of epoxidized fatty acids includes U.S. Pat. No. 4,546,120 to Peerman, et al.; U.S. Pat. No. 4,551,517 to Herold, et al.; U.S. Pat. No. 4,742,087 to Kluth, et al.; U.S. Pat. No. 4,826,944 to Hoefer, et al.; U.S. Pat. No. 4,886,893 to Meffert, et al.; U.S. Pat. No. 5,266,714 to Stoll, et al.; and U.S. Pat. No. 5,302,626 to Hoefer, et al.

The use of clay catalysts is known. For example, U.S. Pat. Nos. 5,750,787 and 5,672,752 to Lai, et al. teach the use of clay catalysts in a process for monoalklating diphenylamine. U.S. Pat. No. 4,474,602 to Markley, et al. teaches the use of clay catalysts in a process for making substituted pyridyl compounds. U.S. Pat. No. 4,133,799 to R. W. Layer teaches the use of clay catalysts to catalyze the reaction of glyoxal with phenols.

In order to overcome the deficiencies found with conventional processes for making oleochemical oil-based polyols, a method for making oleochemical oil-based polyols from epoxidized oleochemical oil is needed for a variety of applications including preparation of, through polyurethane chemistry, of resins for a variety of uses.

SUMMARY OF THE INVENTION

The present invention is the result of the discovery that oleochemical oil-based polyols can be made using an acid activated or acid leached clay by mixing an epoxidized oleochemical oil, alcohol, and acid activated or acid leached clay so the epoxidized oleochemical oil reacts with said mixture to form an oleochemical oil-based polyol, filtering out said clay, stripping off any excess alcohol, and recovering the vegetable oil-based polyol. A further benefit from the process is that the clay can be recovered, recycled, and reused in the process.

The process of the present invention provides a method for making polyols from renewable resources. The oleochemical oil-based polyols can be used to make polyurethane resins which can be used, for example, as cast resins, foams, coatings, adhesives, or to make composites. The oleochemical oil-based polyols have a favorable distribution of hydroxyl groups in the molecule so that when these polyols are reacted with isocyanates to form polyurethanes, crosslinking within the polyurethane is optimized.

DETAILED DESCRIPTION OF THE INVENTION

In the present invention oleochemical oil-based polyols are made by reacting an epoxidized oleochemical oil and an alcohol using an acid activated or acid leached clay. The clay used in the process is filtered out and can be recovered, recycled, and reused in the process.

The clays useful in the process are often referred to as acid activated clays. Preferred clays are acid activated sub-bentonites or bentonites which are characterized by rapid slaking when it is in the air dried state and only a slight swelling when placed in water. They consist predominantly of the clay mineral montmorillonite. The clay can be used in amounts from about 0.5 wt. % to about 20 percent by weight, based upon the weight of the epoxidized oleochemical oil, preferably from about 1 to about 10 wt. % with about 2 wt. % to about 10 wt. %, and 5 wt. % being further preferred.

Commercially available clay catalysts include Filtrol® and Retrol® clays available from Engelhard; Fulcat® 14, Fulmont® 700C, Fulmont® 237, and Fulcat® 22B clays available from Laporte Industries; and Katalysator® K10 clay available from Sud-Chemi. The clay catalysts may contain some water as received. The amount of water has some effect on the rate of the reaction, the hydroxyl number, and the molecular weight of the final product, but it is not considered critical. Retrol F20 clay catalyst is preferred.

The clays are aluminosilicates. The aluminum III cations are bonded to an octahedral arrangement of oxygen anions. Repetition of these $AlO_6$ units in two dimensions forms an octahedral layer. Likewise a tetrahedral layer is formed from $SiO_4$ silicate units. Clays are classified according to the relative number of tetrahedral and octahedral layers. Montmorillonite clays, which have been used in organic chemical applications, have an octahedral layer sandwiched between two tetrahedral layers.

Any epoxidized oleochemical oil may be used in this process. The epoxidized oleochemical oils are derived from triglycerides, such as fatty oils from vegetable, animal or marine animal origin or from free fatty acids. Examples of oils that may be used include, but are not limited to, soybean (or soya bean) oil, safflower oil, linseed oil, corn oil, sunflower oil, olive oil, canola oil, sesame oil, peanut oil, cottonseed oil, palm oil, rapeseed oil, tung oil, beef tallow, lard, castor oil, fish oil, or a blend of any of these oils, although epoxidized soybean oil is preferred. Alternatively, any partially hydrogenated vegetable oils or genetically modified vegetable oils can be used to obtain the desired hydroxyl content. Examples of partially hydrogenated vegetable oils or genetically modified vegetable oils include, but are not limited to, high oleic safflower oil, high oleic soybean oil, high oleic peanut oil, high oleic sunflower oil and high erucic rapeseed oil (crambe oil). The iodine values of these vegetable oils range from about 40 to 240 and more preferably from about 80 to 240. When vegetable oils having lower iodine values are used to make vegetable oil-based polyols, polyols with lower hydroxyl numbers and thus lower viscosities are created. The epoxide content of the epoxidized oleochemical oil is not critical, but it is preferred that it is in the range of about 6.0% by weight to about 7.0% by weight.

Examples of alcohols or alcohol mixtures that may be used in the hydroxylation reaction include, but are not limited to, monoalcohols such a methanol, ethanol, propanol, and butanol. It is desirable to have methanol be part of the alcohol mixture used in the hydroxylation reaction because it is the least expensive alcohol used in the hydroxylation reaction, although its use is not critical. Other alcohol mixtures may also be used so long as the methanol concentration is kept low. In fact, methanol may be used with solvents other than alcohols, such as chloroform, toluene, formic acid, or acetic acid. It is important during the hydroxylation step to always have an excess amount of alcohol present so as to prevent polymerization and the formation of products having higher molecular weight due to the reaction with the polyol product.

The hydroxylation reaction occurs between about 60° and 70° C. The rate of reaction depends upon the concentration and selection of the ingredients. For example, the greater the amount of the catalyst, the faster the reaction. The process conditions do not appear to be critical. As can be appreciated, the faster the reaction, the less opportunity there is for cross-linking, e.g., the reaction of the epoxide with the polyol product.

The oleochemical oil-based polyols made by the method of the present invention can have a viscosity in the range of 1,000-12,000 centipoise at room temperature. The viscosity of these polyols is lower than oleochemical oil-based polyols made by other methods because the method of the present invention minimizes substantial side-reactions, such as polymerization or crosslinking. Still further, the oleochemical oil-based polyols made by the method of the present invention have a hydroxyl content ranging from 110 to 200 mg KOH/g of product, usually in the range of 140 to 180 mg KOH/g of product. Preferably, the polyol has a high hydroxyl content which equals to approximately one hydroxyl group per double bond of the oleochemical oil. Oleochemical oil-based polyols can be made in very high (85% to 95%) and nearly quantitative yields using the process of the present invention.

The following examples are illustrative of the present invention and should not limit the scope of the invention.

EXAMPLE 1

An epoxidized vegetable oil (epoxidized soybean oil having an epoxide content of about 6.8%), an alcohol (156.25 grams of methanol), and a catalyst (12.5 grams of Retrol F-20 clay) were combined in a 500 milliliter glass reaction flask fitted with a reflux condenser and a stirrer. The reactor was then heated to 65° C.±20 C., and the mixture was stirred until the reaction was complete (approximately 2 hours).

The mixture was then filtered through a Whatman #4 filter paper to separate the liquid from the solid catalyst. Next, the remaining alcohol was stripped off, and the recovered product was analyzed by infrared analysis. The result, i.e., the presence of hydroxyl absorption at about 3470 cm$^{-1}$ and the absence of the epoxide groups at 820 to 860 cm$^{-1}$, confirmed that the product was a soy polyol.

EXAMPLES 2–20

The same process as Example 1 was followed, except that the kind of catalyst, the amount of catalyst, the kind of alcohol, the amount of alcohol, and sources of epoxidized soybean oil (EPSO) were varied as shown in Table I. The epoxidized soybean oil was supplied by Union Carbide ("A"), Ferro ("B"), and Witco ("C"), and a comparison is shown in Table II. The characteristics of the catalysts are shown in Table III.

The results show that the process produces soy polyol using a wide range and amount of reactants.

TABLE I

| Example # | EPSO Amt. (g) | Source | Alcohol Kind | Amt. (grms) | Catalyst Kind | Amt. (% by wt.) |
|---|---|---|---|---|---|---|
| 1 | 125 | A | Methanol | 156.25 | Retrol F-20 | 10 |
| 2 | 50 | A | Methanol | 62.5 | Retrol F-1 | 10 |
| 3 | 50 | A | Methanol | 62.5 | Retrol F-24 | 10 |
| 4 | 50 | A | Methanol | 62.5 | Retrol F-6 | 10 |
| 5 | 50 | A | Methanol | 62.5 | Retrol F-20XLM | 10 |
| 6 | 50 | A | Methanol | 62.5 | Retrol 213 | 10 |
| 7 | 50 | A | Methanol | 62.5 | Retrol F-20X | 10 |
| 8 | 50 | A | Methanol | 62.5 | Retrol F-2 | 10 |
| 9 | 100 | A | Methanol | 125 | Retrol F-20XLM | 5 |
| 10 | 100 | A | Methanol | 125 | Retrol F-20XLM | 3 |
| 11 | 50 | A | Methanol | 31 | Retrol F-20 | 10 |
| 12 | 50 | A | Methanol | 15 | Retrol F-20 | 10 |

TABLE I-continued

| Example # | EPSO Amt. (g) | Source | Alcohol Kind | Amt. (grms) | Catalyst Kind | Amt. (% by wt.) |
|---|---|---|---|---|---|---|
| 13 | 100 | B | Methanol | 125 | Retrol F-20 | 3 |
| 14 | 100 | C | Methanol | 125 | Retrol F-20 | 3 |
| 15 | 50 | A | Ethanol | 55 | Retrol F-20 | 10 |
| 16 | 50 | A | Iso Propanol | 60 | Retrol F-20 | 10 |
| 17 | 50 | A | Iso Propanol | 60 | Retrol F-20 | 10 |
| 18 | 100 | A | Methanol | 250 | Retrol F-20 | 5 |
| 19 | 100 | A | Methanol | 250 | Retrol F-20 | 3 |
| 20 | 100 | A | Methanol | 250 | Retrol F-20 | 10 |

TABLE II

Epoxidized Soybean Oils

| Epoxidized Soybean Oil | % Epoxide | Catalyst | Time (hr.) | OH # | Mw (GPC) | % Epoxide Remaining | Viscosity (cps) |
|---|---|---|---|---|---|---|---|
| A | 6.8 | HBF$_4$ | 0.5 | 174 | 2006 | 0.126 | 4275 |
| A | 6.8 | 5% F20 Clay | 4 | 174 | 2040 | 0.031 | 5888 |
| A | 6.8 | 3% F20 Clay | 6 | 161 | 2154 | 0.388 | |
| A | 6.8 | 10% F20 Clay | 4 | 174 | 2684 | 0.116 | |
| B | 6.8 | 5% F6-LM Clay | 4 | 176 | 2212 | 0.05 | |
| B | 6.8 | 2% F20 Clay | 6 | 183 | 1886 | 0.696 | |
| B | 6.8 | 5% F20XLM Clay | 3 | 140 | 3229 | 0.374 | |
| C | 6.8 | 5% F20XLM Clay | 3 | 155 | 2771 | 0.404 | |

A = Union Carbide Flexol EPO
B = Ferro Plastichek 775
C = Witco Drapex 6.8

These results show that polyols can be made from a variety of sources of epoxidized soybean oil and that polyols made by the process of the present invention are similar to those made using a fluoroboric acid catalyst as is taught in Petrovic et al U.S. Pat. No. 6,107,433.

TABLE III

Clay Catalyst Characteristics

| Clay | % Moisture | Residual Acidity (mg KOH/gram) | Surface Area (m$^2$/gm) |
|---|---|---|---|
| F1 | 15 | 7 | 250 |
| F2 | 16 | pH = 7.5 | |
| F6 | 15 max | 10 min. | |
| F6LM | 3 | 15 | 380 |
| F20 | 14 | 20 | 350 |
| F20X | 14 | 12 | 275 |
| F20XLM | 7 | 10 | |
| F24 | 14 | 11 | 400 |

RECYCLE EXAMPLE

The same process was followed as Example 1, using the same amounts of reactants. The filter cake was recovered. 9.44 g of wet cake was dried and recovered. 8.86 g of wet cake was slurried with methanol to wash away the soy polyol, and afterward was again filtered to recover a second filter cake. The second filter cake was also dried and recovered. The dried clay catalyst was then blended together.

Next, following the same procedure as Example 1, 50 g of epoxidized soybean oil, 62.5 g of methanol, and 5 g of the recovered clay catalyst were combined and heated. The result using the recycled clay catalyst was the same as when it was used fresh.

The foregoing embodiments of the present invention have been presented for the purposes of illustration and description. These descriptions and embodiments are not intended to be exhaustive or to limit the invention to the precise form disclosed, and obviously many modifications and variations are possible in light of the above disclosure. The embodiments were chosen and described in order to best explain the principle of the invention and its practical applications to thereby enable others skilled in the art to best utilize the invention in its various embodiments and with various modifications as are suited to the particular use contemplated. It is intended that the invention be defined by the following claims.

What is claimed is:

1. A method of making oleochemical oil-based polyols comprising:

A. Mixing an acid activated or acid leached clay;

B. Adding an epoxidized oleochemical oil, and an alcohol, whereby said epoxidized oleochemical oil reacts at a temperature between 60° C. and 70° C. with said alcohol to form a oleochemical oil-based polyol;

C. Filtering out said clay;

D. Stripping off any excess alcohol; and

E. Recovering the oleochemical oil-based polyol.

2. The method of claim 1 wherein said clay is present in an amount of about 1 to about 10% by weight, based upon the weight of the oleochemical oil.

3. The method of claim 1 wherein said clay is present in an amount of about 2 to about 10% by weight, based upon the weight of the oleochemical oil.

4. The method of claim 1 wherein said clay is present in an amount of about 5% by weight, based upon the weight of the oleochemical oil.

5. The method of claim 1 wherein after said clay is filtered out, it is recycled and reused is said process.

6. The method of claim 1 wherein said alcohol is methanol.

7. The method of claim 1 wherein said alcohol is selected from the group consisting of methanol, ethanol, propanol, and isopropanol.

8. The method of claim 1 wherein the alcohol is present in an amount of from about 50% to about 150% by weight based upon the weight of the epoxidized oleochemical oil.

9. The method of claim 1 wherein the epoxidized oleochemical oil has an epoxide content of about 6.0% to about 7.0%.

10. The method of claim 1 wherein the oleochemical oil-base polyol has a hydroxyl content of about 110 mg KOH/g of polyol to about 200 mg KOH/g of polyol.

11. The method of claim 1 wherein the oleochemical oil-base polyol has a hydroxyl content of about 140 mg KOH/g of polyol to about 180 mg KOH/g of polyol.

* * * * *